(12) United States Patent
Klittich et al.

(10) Patent No.: US 8,470,840 B2
(45) Date of Patent: Jun. 25, 2013

(54) SYNERGISTIC FUNGICIDAL COMPOSITIONS CONTAINING A 5-FLUOROPYRIMIDINE DERIVATIVE FOR FUNGAL CONTROL IN CEREALS

(75) Inventors: Carla J. R. Klittich, Zionsville, IN (US); Beth Lorsbach, Indianapolis, IN (US); Alice Meitl, Lebanon, IN (US); W. John Owen, Carmel, IN (US); Chenglin Yao, Westfield, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 12/871,392

(22) Filed: Aug. 30, 2010

(65) Prior Publication Data

US 2011/0053966 A1 Mar. 3, 2011

Related U.S. Application Data

(60) Provisional application No. 61/238,793, filed on Sep. 1, 2009, provisional application No. 61/248,192, filed on Oct. 2, 2009.

(51) Int. Cl.
*A01N 43/54* (2006.01)
*A01P 3/00* (2006.01)

(52) U.S. Cl.
USPC .......................................... 514/274; 424/405

(58) Field of Classification Search
USPC .......................................................... 514/274
See application file for complete search history.

(56) References Cited

U.S. PATENT DOCUMENTS

2009/0203647 A1* 8/2009 Benko et al. .................... 514/86

* cited by examiner

*Primary Examiner* — Kortney L Klinkel
(74) *Attorney, Agent, or Firm* — C. W. Arnett; Faegre Baker Daniels LLP

(57) ABSTRACT

A fungicidal composition containing a fungicidally effective amount of a) a compound of Formula IA and/or IB and (b) at least one fungicide selected from the group consisting of epoxiconazole, prothioconazole, azoxystrobin, pyraclostrobin, penthiopyrad, isopyrazam, bixafen, boscalid, prochloraz, chlorothalanil, isobutyric acid (3S,6S,7R,8R)-8-benzyl-3-[(3-isobutyryloxymethoxy-4-methoxypyridine-2-carbonyl)-amino]-6-methyl-4,9-dioxo-[1,5]dioxonan-7-yl ester, and (5,8-difluoroquinazolin-4-yl)-{2-[2-fluoro-4-(4-trifluoromethylpyridin-2-yloxy)-phenyl]-ethyl}-amine provides synergistic control of selected fungi.

16 Claims, No Drawings

SYNERGISTIC FUNGICIDAL COMPOSITIONS CONTAINING A 5-FLUOROPYRIMIDINE DERIVATIVE FOR FUNGAL CONTROL IN CEREALS

CROSS REFERENCE TO RELATED APPLICATIONS

This application claims the benefit of U.S. Provisional Patent Application Ser. No. 61/238,793 filed Sep. 1, 2009 and U.S. Provisional Patent Application Ser. No. 61/248,192, filed Oct. 2, 2009, which are expressly incorporated by reference herein.

FIELD OF THE INVENTION

This invention concerns a synergistic fungicidal composition containing (a) a compound of Formula IA and/or IB and (b) at least one fungicide selected from the group consisting of epoxiconazole, prothioconazole, azoxystrobin, pyraclostrobin, penthiopyrad, isopyrazam, bixafen, boscalid, prochloraz, chlorothalonil, isobutyric acid (3S,6S,7R,8R)-8-benzyl-3-[(3-isobutyryloxymethoxy-4-methoxypyridine-2-carbonyl)-amino]-6-methyl-4,9-dioxo-[1,5]dioxonan-7-yl ester, and (5,8-difluoroquinazolin-4-yl)-{2-[2-fluoro-4-(4-trifluoromethylpyridin-2-yloxy)-phenyl]-ethyl}-amine.

BACKGROUND OF THE INVENTION

Fungicides are compounds, of natural or synthetic origin, which act to protect plants against damage caused by fungi. Current methods of agriculture rely heavily on the use of fungicides. In fact, some crops cannot be grown usefully without the use of fungicides. Using fungicides allows a grower to increase the yield and the quality of the crop and consequently, increase the value of the crop. In most situations, the increase in value of the crop is worth at least three times the cost of the use of the fungicide.

However, no one fungicide is useful in all situations and repeated usage of a single fungicide frequently leads to the development of resistance to that and related fungicides. Consequently, research is being conducted to produce fungicides and combinations of fungicides that are safer, that have better performance, that require lower dosages, that are easier to use, and that cost less.

Synergism occurs when the activity of two, or more, compounds exceeds the activities of the compounds when used alone.

SUMMARY OF THE INVENTION

It is an object of this invention to provide synergistic compositions comprising fungicidal compounds. It is a further object of this invention to provide processes that use these synergistic compositions. The synergistic compositions are capable of preventing or curing, or both, diseases caused by fungi of the class Ascomycetes. In addition, the synergistic compositions have improved efficacy against the Ascomycete pathogens, including leaf blotch of wheat. In accordance with this invention, synergistic compositions are provided along with methods for their use.

DETAILED DESCRIPTION OF THE INVENTION

The present invention concerns a synergistic fungicidal mixture comprising an fungicidally effective amount of (a) a compound of Formula IA and/or IB and (b) at least one fungicide selected from the group consisting of epoxiconazole, prothioconazole, azoxystrobin, pyraclostrobin, penthiopyrad, isopyrazam, bixafen, boscalid, prochloraz, chlorothalanil, isobutyric acid (3S,6S,7R,8R)-8-benzyl-3-[(3-isobutyryloxymethoxy-4-methoxypyridine-2-carbonyl)-amino]-6-methyl-4,9-dioxo-[1,5]dioxonan-7-yl ester, and (5,8-difluoroquinazolin-4-yl)-{2-[2-fluoro-4-(4-trifluoromethylpyridin-2-yloxy)-phenyl]-ethyl}-amine.

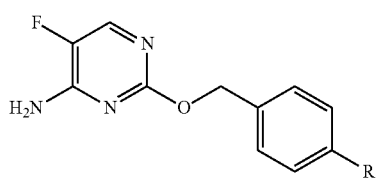

IA, R = CH$_3$
IB, R = F

Epoxiconazole is the common name for rel-1-[[(2R,3S)-3-(2-chlorophenyl)-2-(4-fluorophenyl)oxiranyl]methyl]-1H-1,2,4-triazole. Its fungicidal activity is described in The Pesticide Manual, Fourteenth Edition, 2006. Epoxiconazole provides broad-spectrum fungicidal control, with preventative and curative action, of diseases caused by Ascomycetes, Basidiomycetes and Deuteromycetes in cereals and other crops.

Prothioconazole is the common name for 2-[2-(1-chlorocyclopropyl)-3-(2-chlorophenyl)-2-hydroxypropyl]-1,2-dihydro-3H-1,2,4-triazole-3-thione. Its fungicidal activity is described in The Pesticide Manual, Fourteenth Edition, 2006. Prothioconazole is used for control of diseases such as eyespot, *Fusarium* ear blight, leaf blotch, rust and powdery mildew by foliar application in wheat, barley and other crops.

Azoxystrobin is the common name for methyl (αE)-2-[[6-(2-cyanophenoxy)-4-pyrimidinyl]oxy]-α-(methoxymethylene)benzeneacetate. Its fungicidal activity is described in The Pesticide Manual, Fourteenth Edition, 2006. Azoxystrobin controls a variety of pathogens at application rates between 100 and 375 grams/hectare (g/ha).

Pyraclostrobin is the common name for methyl [2-[[[1-(4-chlorophenyl)-1H-pyrazol-3-yl]oxy]methyl]phenyl]methoxycarbamate. Its fungicidal activity is described in The Pesticide Manual, Fourteenth Edition, 2006. Pyraclostrobin controls major plant pathogens, such as *Septoria tritici, Puccinia* spp., *Drechslera tritici-repentis* and *Pyrenophora teres* in cereals.

Penthiopyrad is the common name for N-[2-(1,3-dimethylbutyl)-3-thienyl]-1-methyl-3-(trifluoromethyl)-1H-pyrazole-4-carboxamide. Its fungicidal activity is described in The Pesticide Manual, Fourteenth Edition, 2006. Penthiopyrad provides control of rust and *Rhizoctonia* diseases, as well as grey mold, powdery mildew and apple scab.

Isopyrazam is the common name for 3-(difluoromethyl)-1-methyl-N-[1,2,3,4-tetrahydro-9-(1-methylethyl)-1,4-methanonaphthalen-5-yl]-1H-pyrazole-4-carboxamide. Its fungicidal activity is described in http://www.agropages.com. Isopyrazam provides control of *Septoria* and rusts in wheat, as well as Ramularia in barley.

Bixafen is the common name for N-(3',4'-dichloro-5-fluoro[1,1'-biphenyl]-2-yl)-3-(difluoromethyl)-1-methyl-1H-pyrazole-4-carboxamide.

Boscalid is the common name for 2-chloro-N-(4'-chloro[1,1'-biphenyl]-2-yl)-3-pyridinecarboxamide. Its fungicidal activity is described in The Pesticide Manual, Fourteenth Edition, 2006. Boscalid provides control of powdery mildew,

*Alternaria* spp., *Botrytis* spp., *Sclerotinia* spp. and *Monilia* spp. on a range of fruit and vegetables.

Prochloraz is the common name for N-propyl-N-[2-(2,4,6-trichlorophenoxy)ethyl]-1H-imidazole-1-carboxamide. Its fungicidal activity is described in The Pesticide Manual, Fourteenth Edition, 2006. Prochloraz acts as a protectant and eradicant fungicide with activity against a wide range of diseases affecting field crops, fruit, turf and vegetables.

Chlorothalonil is the common name for 2,4,5,6-tetrachloro-1,3-benzenedicarbonitrile. Its fungicidal activity is described in The Pesticide Manual, Fourteenth Edition, 2006. Chlorothalonil provides control of many fungal diseases in a wide range of crops.

Isobutyric acid (3S,6S,7R,8R)-8-benzyl-3-[(3-isobutyryloxymethoxy-4-methoxy-pyridine-2-carbonyl)-amino]-6-methyl-4,9-dioxo-[1,5]dioxonan-7-yl ester is shown below as compound A.

Compound A

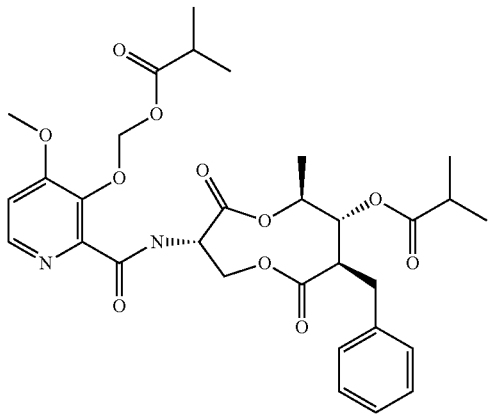

(5,8-Difluoroquinazolin-4-yl)-{2-[2-fluoro-4-(4-trifluoromethylpyridin-2-yloxy)-phenyl]-ethyl}-amine is shown below as compound B, as disclosed in U.S. patent application Ser. No. 12/550,952 filed on Aug. 31, 2009, which is expressly incorporated by reference herein.

Compound B

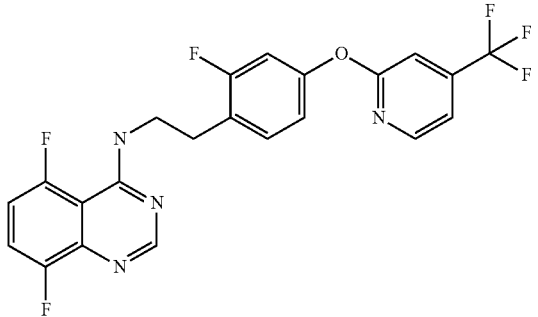

In the composition of this invention, the weight ratio of the compound of Formula IA to epoxiconazole at which the fungicidal effect is synergistic lies within the range of between about 1:4 and about 4:1. The weight ratio of the compound of Formula IA to prothioconazole at which the fungicidal effect is synergistic lies within the range of between about 1:4 and about 4:1. The weight ratio of the compound of Formula IA to azoxystrobin at which the fungicidal effect is synergistic lies within the range of between about 1:4 and about 4:1. The weight ratio of the compound of Formula IA to pyraclostrobin at which the fungicidal effect is synergistic lies within the range of between about 1:4 and about 4:1. The weight ratio of the compound of Formula IA to penthiopyrad at which the fungicidal effect is synergistic lies within the range of between about 1:4 and about 4:1. The weight ratio of the compound of Formula IA to isopyrazam at which the fungicidal effect is synergistic lies within the range of between about 1:4 and about 4:1. The weight ratio of the compound of Formula IA to bixafen at which the fungicidal effect is synergistic lies within the range of between about 1:4 and about 4:1. The weight ratio of the compound of Formula IA to boscalid at which the fungicidal effect is synergistic lies within the range of between about 1:4 and about 4:1. The weight ratio of the compound of Formula IA to prochloraz at which the fungicidal effect is synergistic lies within the range of between about 1:4 and about 4:1. The weight ratio of the compound of Formula IA to chlorothalonil at which the fungicidal effect is synergistic lies within the range of between about 1:1 and about 1:16. The weight ratio of the compound of Formula IA to isobutyric acid (3S,6S,7R,8R)-8-benzyl-3-[(3-isobutyryloxymethoxy-4-methoxypyridine-2-carbonyl)-amino]-6-methyl-4,9-dioxo-[1,5]dioxonan-7-yl ester at which the fungicidal effect is synergistic lies within the range of between about 1:4 and about 4:1. The weight ratio of the compound of Formula IB to (5,8-difluoroquinazolin-4-yl)-{2-[2-fluoro-4-(4-trifluoromethylpyridin-2-yloxy)-phenyl]-ethyl}-amine at which the fungicidal effect is synergistic lies within the range of between about 1:4 and about 4:1.

The rate at which the synergistic composition is applied will depend upon the particular type of fungus to be controlled, the degree of control required and the timing and method of application. In general, the composition of the invention can be applied at an application rate of between about 50 grams per hectare (g/ha) and about 2300 g/ha based on the total amount of active ingredients in the composition. Epoxiconazole is applied at a rate between about 30 g/ha and about 125 g/ha and the compound of Formula IA is applied at a rate between about 20 g/ha and about 300 g/ha. Prothioconazole is applied at a rate between about 50 g/ha and about 200 g/ha and the compound of Formula IA is applied at a rate between about 20 g/ha and about 300 g/ha. Azoxystrobin is applied at a rate between about 50 g/ha and about 250 g/ha and the compound of Formula IA is applied at a rate between about 20 g/ha and about 300 g/ha. Pyraclostrobin is applied at a rate between about 50 g/ha and about 250 g/ha and the compound of Formula IA is applied at a rate between about 20 g/ha and about 300 g/ha. Penthiopyrad is applied at a rate between about 50 g/ha and about 300 g/ha and the compound of Formula IA is applied at a rate between about 20 g/ha and about 300 g/ha. Isopyrazam is applied at a rate between about 30 g/ha and about 125 g/ha and the compound of Formula IA is applied at a rate between about 20 g/ha and about 300 g/ha. Bixafen is applied at a rate between about 50 g/ha and about 300 g/ha and the compound of Formula IA is applied at a rate between about 20 g/ha and about 300 g/ha. Boscalid is applied at a rate between about 50 g/ha and about 350 g/ha and the compound of Formula IA is applied at a rate between about 20 g/ha and about 300 g/ha. Prochloraz is applied at a rate between about 50 g/ha and about 450 g/ha and the compound of Formula IA is applied at a rate between about 20 g/ha and about 300 g/ha. Chlorothalonil is applied at a rate between about 100 g/ha and about 2000 g/ha and the compound of Formula IA is applied at a rate between about 20 g/ha and about 300 g/ha. Isobutyric acid (3S,6S,7R,8R)-8- benzyl-3-[(3-isobutyryloxymethoxy-4-methoxypyridine-2-carbonyl)-amino]-6-methyl-4,9-dioxo-[1,5]dioxonan-7-yl ester is applied at a rate between about 35 g/ha and about 300 g/ha and the compound of Formula IA is applied at a rate between about 20 g/ha and about 300 g/ha. (5,8-Difluoro-quinazolin-4-yl)-{2-[2-fluoro-4-(4-trifluoromethylpyridin-2-yloxy)-phenyl]-ethyl}-amine is applied at a rate between about 50 g/ha and about 300 g/ha and the compound of Formula IB is applied at a rate between about 20 g/ha and about 300 g/ha.

The components of the synergistic mixture of the present invention can be applied either separately or as part of a multipart fungicidal system.

The synergistic mixture of the present invention can be applied in conjunction with one or more other fungicides to control a wider variety of undesirable diseases. When used in conjunction with other fungicide(s), the presently claimed compounds may be formulated with the other fungicide(s), tank mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis, Bacillus subtilis* strain QST713, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)-N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

The compositions of the present invention are preferably applied in the form of a formulation comprising a composition of (a) a compound of Formula IA and/or IB and (b) at least one fungicide selected from the group consisting of epoxiconazole, prothioconazole, azoxystrobin, pyraclostrobin, penthiopyrad, isopyrazam, bixafen, boscalid, prochloraz, chlorothalanil, isobutyric acid (3S,6S,7R,8R)-8-benzyl-3-[(3-isobutyryloxymethoxy-4-methoxypyridine-2- carbonyl)-amino]-6-methyl-4,9-dioxo-[1,5]dioxonan-7-yl ester, and (5,8-difluoroquinazolin-4-yl)-{2-[2-fluoro-4-(4-trifluoromethylpyridin-2-yloxy)-phenyl]-ethyl}-amine, together with a phytologically acceptable carrier.

Concentrated formulations can be dispersed in water, or another liquid, for application, or formulations can be dust-like or granular, which can then be applied without further treatment. The formulations are prepared according to procedures which are conventional in the agricultural chemical art, but which are novel and important because of the presence therein of a synergistic composition.

The formulations that are applied most often are aqueous suspensions or emulsions. Either such water-soluble, water suspendable, or emulsifiable formulations are solids, usually known as wettable powders, or liquids, usually known as emulsifiable concentrates, aqueous suspensions, or suspension concentrates. The present invention contemplates all vehicles by which the synergistic compositions can be formulated for delivery and use as a fungicide.

As will be readily appreciated, any material to which these synergistic compositions can be added may be used, provided they yield the desired utility without significant interference with the activity of these synergistic compositions as antifungal agents.

Wettable powders, which may be compacted to form water dispersible granules, comprise an intimate mixture of the synergistic composition, a carrier and agriculturally acceptable surfactants. The concentration of the synergistic composition in the wettable powder is usually from about 10% to about 90% by weight, more preferably about 25% to about 75% by weight, based on the total weight of the formulation. In the preparation of wettable powder formulations, the synergistic composition can be compounded with any of the finely divided solids, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier is ground or mixed with the synergistic composition in a volatile organic solvent. Effective surfactants, comprising from about 0.5% to about 10% by weight of the wettable powder, include sulfonated lignins, naphthalenesulfonates, alkylbenzenesulfonates, alkyl sulfates, and non-ionic surfactants, such as ethylene oxide adducts of alkyl phenols.

Emulsifiable concentrates of the synergistic composition comprise a convenient concentration, such as from about 10% to about 50% by weight, in a suitable liquid, based on the total weight of the emulsifiable concentrate formulation. The components of the synergistic compositions, jointly or separately, are dissolved in a carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil soluble salts or sulphated polyglycol ethers and appropriate salts of phosphated polyglycol ether.

Representative organic liquids which can be employed in preparing the emulsifiable concentrates of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol. Mixtures of two or more organic liquids are also often suitably employed in the preparation of the emulsifiable concentrate. The preferred organic liquids are xylene, and propyl benzene fractions, with xylene being most preferred. The surface-active dispersing agents are usually employed in liquid formulations and in the amount of from 0.1 to 20 percent by weight of the combined weight of the dispersing agent with the synergistic compositions. The formulations can also contain other compatible additives, for example, plant growth regulators and other biologically active compounds used in agriculture.

Aqueous suspensions comprise suspensions of one or more water-insoluble compounds, dispersed in an aqueous vehicle at a concentration in the range from about 5% to about 70% by weight, based on the total weight of the aqueous suspension formulation. Suspensions are prepared by finely grinding the components of the synergistic combination either together or separately, and vigorously mixing the ground material into a vehicle comprised of water and surfactants chosen from the same types discussed above. Other ingredients, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

The synergistic composition may also be applied as granular formulation, which is particularly useful for applications to the soil. Granular formulations usually contain from about 0.5% to about 10% by weight of the compounds, based on the total weight of the granular formulation, dispersed in a carrier which consists entirely or in large part of coarsely divided attapulgite, bentonite, diatomite, clay or a similar inexpensive substance. Such formulations are usually prepared by dissolving the synergistic composition in a suitable solvent and applying it to a granular carrier which has been preformed to the appropriate particle size, in the range of from about 0.5 to about 3 mm. Such formulations may also be prepared by making a dough or paste of the carrier and the synergistic composition, and crushing and drying to obtain the desired granular particle.

Dusts containing the synergistic composition are prepared simply by intimately mixing the synergistic composition in powdered form with a suitable dusty agricultural carrier, such as, for example, kaolin clay, ground volcanic rock, and the like. Dusts can suitably contain from about 1% to about 10% by weight of the synergistic composition/carrier combination.

The formulations may contain agriculturally acceptable adjuvant surfactants to enhance deposition, wetting and penetration of the synergistic composition onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5 percent. Suitable adjuvant surfactants include ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

The formulations may optionally include combinations that can comprise at least 1% by weight of one or more of the synergistic compositions with another pesticidal compound. Such additional pesticidal compounds may be fungicides, insecticides, nematocides, miticides, arthropodicides, bactericides or combinations thereof that are compatible with the synergistic compositions of the present invention in the medium selected for application, and not antagonistic to the activity of the present compounds. Accordingly, in such embodiments the other pesticidal compound is employed as a supplemental toxicant for the same or for a different pesticidal use. The pesticidal compound and the synergistic composition can generally be mixed together in a weight ratio of from 1:100 to 100:1.

The present invention includes within its scope methods for the control or prevention of fungal attack. These methods comprise applying to the locus of the fungus, or to a locus in which the infestation is to be prevented (for example applying to wheat or barley plants), a fungicidally effective amount of the synergistic composition. The synergistic composition is suitable for treatment of various plants at fungicidal levels, while exhibiting low phytotoxicity. The synergistic composition is useful in a protectant or eradicant fashion. The synergistic composition is applied by any of a variety of known techniques, either as the synergistic composition or as a formulation comprising the synergistic composition. For example, the synergistic compositions may be applied to the roots, seeds or foliage of plants for the control of various fungi, without damaging the commercial value of the plants. The synergistic composition is applied in the form of any of the generally used formulation types, for example, as solutions, dusts, wettable powders, flowable concentrates, or emulsifiable concentrates. These materials are conveniently applied in various known fashions.

The synergistic composition has been found to have significant fungicidal effect particularly for agricultural use. The synergistic composition is particularly effective for use with agricultural crops and horticultural plants, or with wood, paint, leather or carpet backing.

In particular, the synergistic composition is effective in controlling a variety of undesirable fungi that infect useful plant crops. The synergistic composition can be used against a variety of Ascomycete fungi, including for example the following representative fungi species: leaf blotch of wheat (*Mycosphaerella graminicola*; anamorph: *Septoria tritici*; Bayer code SEPTTR); glume blotch of wheat (*Leptosphaeria nodorum*; Bayer code LEPTNO; anamorph: *Stagonospora nodorum*); spot blotch of barley (*Cochliobolus sativum*; Bayer code COCHSA; anamorph: *Helminthosporium sativum*); leaf spot of sugar beets (*Cercospora beticola*; Bayer code CERCBE); leaf spot of peanut (*Mycosphaerella arachidis*; Bayer code MYCOAR; anamorph: *Cercospora arachidicola*); cucumber anthracnose (*Glomerella lagenarium*; anamorph: *Colletotrichum lagenarium*; Bayer code COLLLA); apple scab (*Venturia inaequalis*; Bayer code VENTIN); and black sigatoka disease of banana (*Mycosphaerella fijiensis*; BAYER code MYCOFI). It will be understood by those in the art that the efficacy of the synergistic compositions for one or more of the foregoing fungi establishes the general utility of the synergistic compositions as fungicides.

The synergistic compositions have a broad range of efficacy as a fungicide. The exact amount of the synergistic composition to be applied is dependent not only on the relative amounts of the components, but also on the particular action desired, the fungal species to be controlled, and the stage of growth thereof, as well as the part of the plant or other product to be contacted with the synergistic composition. Thus, formulations containing the synergistic composition may not be equally effective at similar concentrations or against the same fungal species.

The synergistic compositions are effective in use with plants in a disease inhibiting and phytologically acceptable amount. The term "disease inhibiting and phytologically acceptable amount" refers to an amount of the synergistic composition that kills or inhibits the plant disease for which control is desired, but is not significantly toxic to the plant. This amount will generally be from about 1 to about 1000 ppm, with about 2 to about 500 ppm being preferred. The exact concentration of synergistic composition required varies with the fungal disease to be controlled, the type of formulation employed, the method of application, the particular plant species, climate conditions, and the like. A suitable application rate for the synergistic composition typically corresponds to about 0.10 to about 4 pounds/acre (about 0.1 to 0.45 grams per square meter g/m2).

The present compositions can be applied to fungi or their locus by the use of conventional ground sprayers, granule applicators, and by other conventional means known to those skilled in the art.

The following examples are provided to further illustrate the invention. They are not meant to be construed as limiting the invention.

EXAMPLES

Evaluation of Curative and Protectant Activity of Fungicide Mixtures vs. Leaf Blotch of Wheat (*Mycosphaerella graminicola*; anamorph: *Septoria tritici*; Bayer code: SEPTTR)

Wheat plants (variety Yuma) were grown from seed in a greenhouse in plastic pots with a surface area of 27.5 square centimeters (cm2) containing 50% mineral soil/50% soil-less Metro mix, with 8-12 seedlings per pot. The plants were employed for testing when the first leaf was fully emerged, which typically took 7 to 8 days after planting. Test plants were inoculated with an aqueous spore suspension of Septoria tritici either 3-days prior to (3-day curative test; 3DC) or 1-day after fungicide treatments (1-day protectant test; 1DP). After inoculation the plants were kept at 100% relative humidity (one day in a dark dew chamber followed by two days in a lighted mist chamber) to permit spores to germinate and infect the leaf. The plants were then transferred to a greenhouse until disease symptoms were fully expressed.

For the mixture studies with compound of Formula IA: Treatments consisted of fungicides, including a compound of Formula IA, epoxiconazole, prothioconazole, azoxystrobin, pyraclostrobin, penthiopyrad, isopyrazam, bixafen, boscalid, prochloraz, chlorothalonil, and isobutyric acid (3S,6S,7R,8R)-8-benzyl-3-[(3-isobutyryloxymethoxy-4-methoxypyridine-2-carbonyl)-amino]-6-methyl-4,9-dioxo-[1,5]dioxonan-7-yl ester (compound A), applied either individually or as two-way mixtures with a compound of Formula IA. Technical grades of materials were dissolved in acetone to make stock solutions, which were then used to perform three-fold dilutions in acetone either for each individual fungicide component or for the two-way mixtures. Desired fungicide rates were obtained after mixing dilutions with nine volumes of water containing 110 parts per million (ppm) Triton X-100.

Ten mL fungicide solutions were applied onto six pots of plants using an automated booth sprayer, which utilized two 6218-1/4 JAUPM spray nozzles operating at 20 pounds per square inch (psi) set at opposing angles to cover both leaf surfaces. All sprayed plants were allowed to air dry prior to further handling. Control plants were sprayed in the same manner with the solvent blank.

For the mixture studies with compound of Formula IB: Compound IB and the compound B or their two-way mixtures were diluted in three-fold series using suspension concentrate (SC) formulations in 0.1% Trycol 5941. Spray solutions were applied onto plants using a track sprayer with an application volume of 200 Liters/hectare (L/Ha).

When disease reached 80 to 100% on the control plants, infection levels were assessed on treated plants visually and scored on a scale of 0 to 100 percent. Percentage of disease control was then calculated using the ratio of disease on treated plants relative to control plants.

Colby's equation was used to determine the fungicidal effects expected from the mixtures. (See Colby, S. R. Calculation of the synergistic and antagonistic response of herbicide combinations. Weeds 1967, 15, 20-22.)

The following equation was used to calculate the expected activity of mixtures containing two active ingredients, A and B:

$$\text{Expected} = A + B - (A \times B/100)$$

A=observed efficacy of active component A at the same concentration as used in the mixture;
B=observed efficacy of active component B at the same concentration as used in the mixture.

Treatments evaluated, application rate employed, pathogens evaluated and resulting disease control are presented in the following Tables 1-12.

% DC Obs=Percent disease control observed
% DC Exp=Percent disease control expected

TABLE 1

Synergistic interactions of compound IA and epoxiconazole in 1-day protectant (1DP) and 3-day curative (3DC) *Septoria tritici* (SEPTTR) tests

| Application rate (ppm) | | 3DC SEPTTR | | 1DP SEPTTR | |
|---|---|---|---|---|---|
| Compound IA | Epoxiconazole | % DC Obs | % DC exp | % DC Obs | % DC exp |
| 0.3 | | 10 | — | 0 | — |
| 0.1 | | 4 | — | 3 | — |
| | 0.375 | 46 | — | 83 | — |
| | 0.125 | 18 | — | 2 | — |
| 0.3 | 0.375 | 76 | 51 | 88 | 83 |
| 0.1 | 0.125 | 26 | 21 | 13 | 5 |

TABLE 2

Synergistic interactions of compound IA and prothioconazole in 1DP and 3DC SEPTTR tests

| Application rate (ppm) | | 3DC SEPTTR | | 1DP SEPTTR | |
|---|---|---|---|---|---|
| Compound IA | Prothioconazole | % DC Obs | % DC exp | % DC Obs | % DC exp |
| 2.8 | | 94 | — | 85 | — |
| 0.9 | | 44 | — | 22 | — |
| 0.3 | | 10 | — | 0 | — |
| | 5.6 | 20 | — | 25 | — |
| | 1.8 | 8 | — | 2 | — |
| | 0.6 | 10 | — | 2 | — |
| 2.8 | 5.6 | 95 | 95 | 97 | 89 |
| 0.9 | 1.8 | 72 | 48 | 42 | 23 |
| 0.3 | 0.6 | 68 | 19 | 5 | 2 |

TABLE 3

Synergistic interactions of compound IA and azoxystrobin in 1DP and 3DC SEPTTR tests

| Application rate (ppm) | | 3DC SEPTTR | | 1DP SEPTTR | |
|---|---|---|---|---|---|
| Compound IA | Azoxystrobin | % DC Obs | % DC exp | % DC Obs | % DC exp |
| 2.8 | | 94 | — | 85 | — |
| 0.9 | | 44 | — | 22 | — |
| 0.3 | | 10 | — | 0 | — |
| | 5.6 | 20 | — | 33 | — |
| | 1.8 | 14 | — | 3 | — |
| | 0.6 | 10 | — | 3 | — |
| 2.8 | 5.6 | 99 | 95 | 99 | 90 |
| 0.9 | 1.8 | 85 | 52 | 45 | 24 |
| 0.3 | 0.6 | 42 | 19 | 10 | 3 |

TABLE 4

Synergistic interactions of compound IA and pyraclostrobin in 1DP and 3DC SEPTTR tests

| Application rate (ppm) | | 3DC SEPTTR | | 1DP SEPTTR | |
|---|---|---|---|---|---|
| Compound IA | Pyraclostrobin | % DC Obs | % DC exp | % DC Obs | % DC exp |
| 0.3 | | 10 | — | 0 | — |
| 0.1 | | 4 | — | 3 | — |
| 0.03 | | 2 | — | 2 | — |
| | 0.6 | 92 | — | 95 | — |
| | 0.2 | 22 | — | 62 | — |
| | 0.06 | 2 | — | 15 | — |
| 0.3 | 0.6 | 100 | 92 | 98 | 95 |
| 0.1 | 0.2 | 87 | 25 | 72 | 63 |
| 0.03 | 0.06 | 36 | 4 | 17 | 16 |

TABLE 5

Synergistic interactions of compound IA and penthiopyrad in 1DP and 3DC SEPTTR tests

| Application rate (ppm) | | 3DC SEPTTR | | 1DP SEPTTR | |
|---|---|---|---|---|---|
| Compound IA | Penthiopyrad | % DC Obs | % DC exp | % DC Obs | % DC exp |
| 0.9 | | 44 | — | 22 | — |
| 0.3 | | 10 | — | 0 | — |
| 0.1 | | 4 | — | 3 | — |

TABLE 5-continued

Synergistic interactions of compound IA and penthiopyrad in 1DP and 3DC SEPTTR tests

| Application rate (ppm) | | 3DC SEPTTR | | 1DP SEPTTR | |
|---|---|---|---|---|---|
| Compound IA | Penthio-pyrad | % DC Obs | % DC exp | % DC Obs | % DC exp |
| | 1.8 | 4 | — | 17 | — |
| | 0.6 | 4 | — | 10 | — |
| | 0.2 | 8 | — | 2 | — |
| 0.9 | 1.8 | 85 | 46 | 57 | 35 |
| 0.3 | 0.6 | 85 | 14 | 13 | 10 |
| 0.1 | 0.2 | 60 | 12 | 0 | 5 |

TABLE 6

Synergistic interactions of compound IA and isopyrazam in 1DP and 3DC SEPTTR tests

| Application rate (ppm) | | 3DC SEPTTR | | 1DP SEPTTR | |
|---|---|---|---|---|---|
| Compound IA | Iso-pyrazam | % DC Obs | % DC exp | % DC Obs | % DC exp |
| 0.9 | | 44 | — | 22 | — |
| 0.3 | | 10 | — | 0 | — |
| | 1.8 | 18 | — | 23 | — |
| | 0.6 | 10 | — | 15 | — |
| 0.9 | 1.8 | 76 | 54 | 67 | 40 |
| 0.3 | 0.6 | 74 | 19 | 20 | 15 |

TABLE 7

Synergistic interactions of compound IA and bixafen in 1DP and 3DC SEPTTR tests

| Application rate (ppm) | | 3DC SEPTTR | | 1DP SEPTTR | |
|---|---|---|---|---|---|
| Compound IA | Bixafen | % DC Obs | % DC exp | % DC Obs | % DC exp |
| 0.9 | | 44 | — | 22 | — |
| 0.3 | | 10 | — | 0 | — |
| 0.1 | | 4 | — | 3 | — |
| | 1.8 | 14 | — | 12 | — |
| | 0.6 | 4 | — | 7 | — |
| | 0.2 | 6 | — | 3 | — |
| 0.9 | 1.8 | 58 | 52 | 57 | 31 |
| 0.3 | 0.6 | 46 | 14 | 12 | 7 |
| 0.1 | 0.2 | 40 | 10 | 0 | 7 |

TABLE 8

Synergistic interactions of compound IA and boscalid in 1DP and 3DC SEPTTR tests

| Application rate (ppm) | | 3DC SEPTTR | | 1DP SEPTTR | |
|---|---|---|---|---|---|
| Compound IA | Boscalid | % DC Obs | % DC exp | % DC Obs | % DC exp |
| 2.8 | | 94 | — | 85 | — |
| 0.9 | | 44 | — | 22 | — |
| | 5.6 | 34 | — | 30 | — |
| | 1.8 | 12 | — | 5 | — |
| 2.8 | 5.6 | 96 | 96 | 95 | 90 |
| 0.9 | 1.8 | 74 | 51 | 38 | 26 |

TABLE 9

Synergistic interactions of compound IA and prochloraz in 1DP and 3DC SEPTTR tests

| Application rate (ppm) | | 3DC SEPTTR | | 1DP SEPTTR | |
|---|---|---|---|---|---|
| Compound IA | Prochloraz | % DC Obs | % DC exp | % DC Obs | % DC exp |
| 2.8 | | 94 | — | 85 | — |
| 0.9 | | 44 | — | 22 | — |
| | 5.6 | 22 | — | 33 | — |
| | 1.8 | 24 | — | 10 | — |
| 2.8 | 5.6 | 99 | 95 | 98 | 90 |
| 0.9 | 1.8 | 89 | 57 | 72 | 30 |

TABLE 10

Synergistic interactions of compound IA and chlorothalanil in 1DP and 3DC SEPTTR tests

| Application rate (ppm) | | 3DC SEPTTR | | 1DP SEPTTR | |
|---|---|---|---|---|---|
| Compound IA | Chloro-thalanil | % DC Obs | % DC exp | % DC Obs | % DC exp |
| 8.3 | | 100 | — | 98 | — |
| 2.8 | | 94 | — | 85 | — |
| 0.9 | | 44 | — | 22 | — |
| | 125 | 6 | — | 0 | — |
| | 42 | 4 | — | 2 | — |
| | 13.5 | 4 | — | 0 | — |
| 8.3 | 125 | 99 | 100 | 100 | 98 |
| 2.8 | 42 | 96 | 94 | 88 | 85 |
| 0.9 | 13.5 | 54 | 46 | 23 | 22 |

TABLE 11

Synergistic interactions of compound IA and compound A in 1DP and 3DC SEPTTR tests

| Application rate (ppm) | | 3DC SEPTTR | | 1DP SEPTTR | |
|---|---|---|---|---|---|
| Compound IA | Compound A | % DC Obs | % DC exp | % DC Obs | % DC exp |
| 0.9 | | 44 | — | 22 | — |
| 0.3 | | 10 | — | 0 | — |
| | 1.35 | 52 | — | 80 | — |
| | 0.45 | 22 | — | 3 | — |
| 0.9 | 1.35 | 93 | 73 | 100 | 84 |
| 0.3 | 0.45 | 38 | 30 | 37 | 3 |

TABLE 12

Synergistic interactions of compound IB and compound B in 1DP and 3DC SEPTTR tests

| Application rate (g ai/Ha) | | 3DC SEPTTR | | 1DP SEPTTR | |
|---|---|---|---|---|---|
| Compound IB | Compound B | % DC Obs | % DC exp | % DC Obs | % DC exp |
| 1.5 | | 74 | — | 46 | — |
| | 1.5 | 41 | — | 36 | — |
| 1.5 | 1.5 | 95 | 85 | 90 | 65 | g ai/ha—grams of active ingredient per hectare

What is claimed:

1. A synergistic fungicidal mixture comprising a fungicidally effective amount of a) a compound of Formula IA and (b) at least one fungicide selected from the group consisting of epoxiconazole, prothioconazole, azoxystrobin, pyraclostrobin, penthiopyrad, isopyrazam, bixafen, boscalid, prochloraz, chlorothalanil, and isobutyric acid (3S,6S,7R,8R)-8-benzyl-3-[(3-isobutyryloxymethoxy-4-methoxypyridine-2-carbonyl)-amino]-6-methyl-4,9-dioxo-[1,5]dioxonan-7-yl ester.

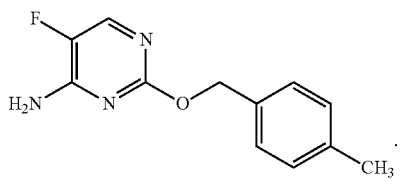

IA

2. The mixture of claim 1 in which the weight ratio of the compound of Formula IA to epoxiconazole is between about 1:4 and about 4:1.

3. The mixture of claim 1 in which the weight ratio of the compound of Formula IA to prothioconazole is between about 1:4 and about 4:1.

4. The mixture of claim 1 in which the weight ratio of the compound of Formula IA to azoxystrobin is between about 1:4 and about 4:1.

5. The mixture of claim 1 in which the weight ratio of the compound of Formula IA to pyraclostrobin is between about 1:4 and about 4:1.

6. The mixture of claim 1 in which the weight ratio of the compound of Formula IA to penthiopyrad is between about 1:4 and about 4:1.

7. The mixture of claim 1 in which the weight ratio of the compound of Formula IA to isopyrazam is between about 1:4 and about 4:1.

8. The mixture of claim 1 in which the weight ratio of the compound of Formula IA to bixafen is between about 1:4 and about 4:1.

9. The mixture of claim 1 in which the weight ratio of the compound of Formula IA to boscalid is between about 1:4 and about 4:1.

10. The mixture of claim 1 in which the weight ratio of the compound of Formula IA to prochloraz is between about 1:4 and about 4:1.

11. The mixture of claim 1 in which the weight ratio of the compound of Formula IA to chlorothalanil is between about 1:1 and about 1:16.

12. The mixture of claim 1 in which the weight ratio of the compound of Formula IA to isobutyric acid (3S,6S,7R,8R)-8-benzyl-3-[(3-isobutyryloxymethoxy-4-methoxypyridine-2-carbonyl)-amino]-6-methyl-4,9-dioxo-[1,5]dioxonan-7-yl ester is between about 1:4 and about 4:1.

13. A fungicidal composition comprising a fungicidally effective amount of the fungicidal mixture of claim 1 and an agriculturally acceptable adjuvant or carrier.

14. A synergistic fungicidal mixture comprising a fungicidally effective amount of a) a compound of Formula IB and b) (5,8-difluoroquinazolin-4-yl)-{2-[2-fluoro-4-(4-trifluoromethylpyridin-2-yloxy)-phenyl]-ethyl}-amine.

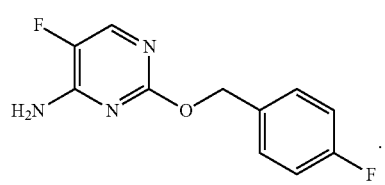

IB

15. The mixture of claim 14 in which the weight ratio of the compound of Formula IB to (5,8-difluoroquinazolin-4-yl)-{2-[2-fluoro-4-(4-trifluoromethylpyridin-2-yloxy)-phenyl]-ethyl}-amine is between about 1:4 and about 4:1.

16. A fungicidal composition comprising a fungicidally effective amount of the fungicidal mixture of claim 14 and an agriculturally acceptable adjuvant or carrier.

* * * * *